United States Patent
Wu et al.

(10) Patent No.: US 10,433,985 B2
(45) Date of Patent: Oct. 8, 2019

(54) LIMB PROSTHESIS

(71) Applicant: Industrial Technology Research Institute, Hsinchu (TW)

(72) Inventors: Tzong-Ming Wu, Taipei (TW); Ji-Bin Horng, Tainan (TW); Sung-Ho Liu, Kaohsiung (TW); Tsung-Wen Tsai, New Taipei (TW)

(73) Assignee: Industrial Technology Research Institute Hsinchu (TW)

( * ) Notice: Subject to any disclaimer, the term of this patent is extended or adjusted under 35 U.S.C. 154(b) by 137 days.

(21) Appl. No.: 15/844,648

(22) Filed: Dec. 18, 2017

(65) Prior Publication Data
US 2019/0175363 A1 Jun. 13, 2019

(30) Foreign Application Priority Data
Dec. 8, 2017 (TW) .............................. 106143102 A

(51) Int. Cl.
*A61F 2/56* (2006.01)
*A61F 2/58* (2006.01)
(Continued)

(52) U.S. Cl.
CPC .............. *A61F 2/585* (2013.01); *A61F 2/582* (2013.01); *A61F 2/80* (2013.01);
(Continued)

(58) Field of Classification Search
CPC ... A61F 2/582; A61F 2/585; A61F 2002/6854
(Continued)

(56) References Cited

U.S. PATENT DOCUMENTS
6,361,570 B1   3/2002   Gow

FOREIGN PATENT DOCUMENTS
CN   204636627        9/2015
DE       354244    *   6/1922   .............. A61F 2/582
(Continued)

OTHER PUBLICATIONS

Ian Birrell, "3D-printed prosthetic limbs: the next revolution in medicine," Feb. 19, 2017, available at: https://www.theguardian.com/technology/2017/feb/19/3d-printedprosthetic-limbs-revolution-inmedicine.

(Continued)

*Primary Examiner* — David H Willse
(74) *Attorney, Agent, or Firm* — JCIPRNET

(57) ABSTRACT

A limb prosthesis including a palm, a forearm, an upper arm, an elbow joint and a wrist joint is provided. The palm has a first pivot and a first lock set. The upper arm has a socket. The elbow joint connects the forearm to the upper arm. The wrist joint includes a first connecting rod connected to the forearm. The first pivot rotatably penetrates through the first connecting rod. The first lock set is locked to the first pivot. A first wedge surface of the first lock set contacts a second wedge surface of the first connecting rod. By adjusting a distance between the first lock set and the first pivot, a magnitude of a forward force between the first wedge surface and the second wedge surface is adjusted, such that the palm is fixed relative to the first connecting rod or rotatable around an axial direction perpendicular to an extending direction of the forearm.

16 Claims, 8 Drawing Sheets

(51) Int. Cl.
A61F 2/80 (2006.01)
A61F 2/50 (2006.01)
A61F 2/68 (2006.01)

(52) U.S. Cl.
CPC . *A61F 2002/502* (2013.01); *A61F 2002/5041* (2013.01); *A61F 2002/5043* (2013.01); *A61F 2002/6854* (2013.01)

(58) Field of Classification Search
USPC .................................................. 623/59–62
See application file for complete search history.

(56) References Cited

FOREIGN PATENT DOCUMENTS

| TW | M253330 | 12/2004 |
|---|---|---|
| TW | M257179 | 2/2005 |
| TW | M478429 | 5/2014 |
| TW | M522010 | 5/2016 |

OTHER PUBLICATIONS

Jorge Zuniga et al., "Cyborg beast: a low-cost 3d-printed prosthetic hand for children with upper-limb differences," BMC Research Notes, vol. 8, No. 10, Jan. 20, 2015, pp. 1-8.

Jonathan Schwartz., "The future of 3D-printed prosthetics," Jun. 26, 2016, available at: https://techcrunch.com/2016/06/26/the-future-of-3d-printedprosthetics/.

* cited by examiner

LIMB PROSTHESIS

CROSS-REFERENCE TO RELATED APPLICATION

This application claims the priority benefit of Taiwan application serial no. 106143102, filed on Dec. 8, 2017. The entirety of the above-mentioned patent application is hereby incorporated by reference herein and made a part of this specification.

BACKGROUND OF THE DISCLOSURE

Field of the Disclosure

The disclosure relates to a limb prosthesis, and particularly relates to a limb prosthesis including a wrist joint.

Description of Related Art

Regarding the use of medical assistive devices sold in the market, a doctor may select a product with a proper size from products of particular sizes provided by medical device manufacturers based on the needs of a patient, as ordinary people shop for clothes. If a customized limb prosthesis is required, a prosthesis technician has to take a mold, produce the product and perform correction and adjustment. Along with evolution of the times, on one hand, technicians with professional experiences are more and more difficult to find; on the other hand, medical device manufacturers provide diversified product design options in a standardized mass production manner, so as to reduce cost and time for obtaining the limb prostheses. The medical device manufacturers provide doctors and most of the patients with although not satisfied but acceptable solutions. But some patients, such as young children, may be an overlooked group, which is not a target market for the medical device manufacturers. A growing child needs a made-to-measure limb prosthesis coordinating with different growth stages. Moreover, the limb prostheses sold in the market generally adopt the design of a fixed wrist, which is inflexible in usage for an adult, and for a young child using the same, it is hard to perform body coordination exercises in a sitting posture, a kneeling posture and a lying posture, and is not easy to rehabilitate its proprioception and limb muscle strength.

Although there are mechanical limb prostheses available in the market that may provide a motive power and fine motor control, they have a high price and high operation complexity, and are not adapted to growing young children requiring the limb prostheses.

SUMMARY OF THE DISCLOSURE

The disclosure provides a limb prosthesis including a palm, a forearm, an upper arm, an elbow joint and a wrist joint. The palm has a first pivot and a first lock set. The upper arm has a socket. The elbow joint connects the forearm to the upper arm. The wrist joint connects the palm to the forearm. The wrist joint includes a first connecting rod. The first connecting rod is connected to the forearm. The first pivot rotatably penetrates through the first connecting rod. The first lock set is locked to the first pivot. A first wedge surface of the first lock set is used for contacting a second wedge surface of the first connecting rod. By adjusting a distance between the first lock set and the first pivot, a magnitude of a forward force between the first wedge surface and the second wedge surface is adjusted, such that the palm is fixed relative to the first connecting rod or rotatable around an axial direction. The axial direction is perpendicular to an extending direction of the forearm.

The disclosure provides another limb prosthesis including a palm, a forearm and a wrist joint. The palm has a pivot and a lock set. The forearm has a socket. The wrist joint connects the palm to the forearm. The wrist joint includes a first connecting rod. The first connecting rod is connected to the forearm. The pivot rotatably penetrates through the first connecting rod. The lock set is locked to the pivot. A first wedge surface of the lock set is used for contacting a second wedge surface of the first connecting rod. By adjusting a distance between the lock set and the pivot, a magnitude of a forward force between the first wedge surface and the second wedge surface is adjusted, such that the palm is fixed relative to the first connecting rod or rotatable around an axial direction. The axial direction is perpendicular to an extending direction of the forearm.

In order to make the aforementioned and other features and advantages of the disclosure comprehensible, several exemplary embodiments accompanied with figures are described in detail below.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

DESCRIPTION OF EMBODIMENTS

Figure 1:
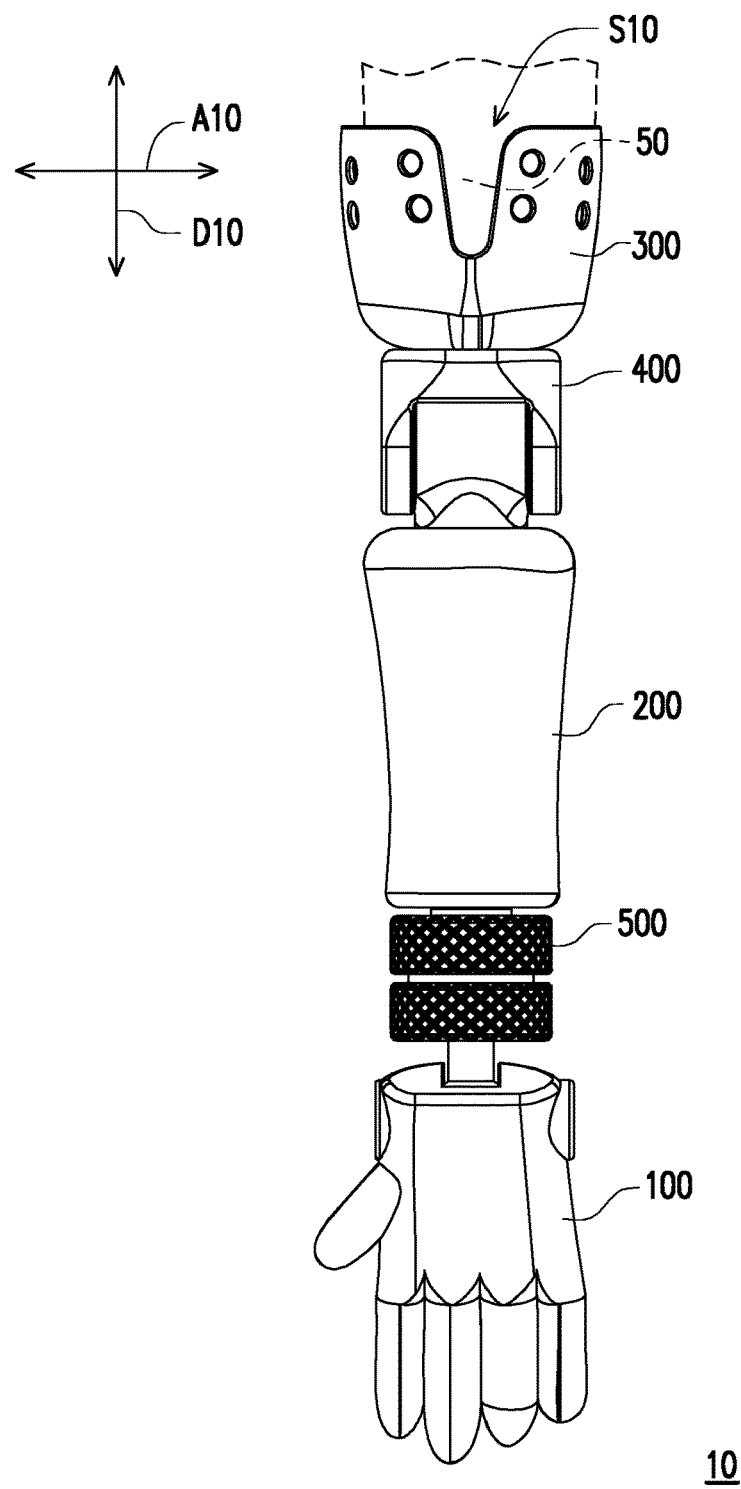
FIG. 1 is a schematic diagram of a limb prosthesis according to an embodiment of the disclosure.

FIG. 1 is a schematic diagram of a limb prosthesis according to an embodiment of the disclosure. Referring to FIG. 1, the limb prosthesis 10 of the present embodiment includes a palm 100, a forearm 200, an upper arm 300, an elbow joint 400 and a wrist joint 500. The upper arm 300 has a socket S10. The socket S10 is used for accepting a stump 50 of a user. The stump 50 of the user accepted by the socket S10 of the present embodiment is a residual limb of an upper arm of the user. The elbow joint 400 connects the forearm 200 to the upper arm 300. The wrist joint 500 connects the palm 100 to the forearm 200. The palm 100 is adapted to rotate and fix relative to the forearm 200 through the wrist joint 500 around an axial direction A10, where the axial direction A10 is perpendicular to an extending direction D10 of the forearm 200. In other words, the palm 100 of the limb prosthesis 10 may perform flexion and extension relative to the forearm 200 as that does of a healthy person. Moreover, after the palm 100 of the limb prosthesis 10 is flexed or extended to a desired rotation angle relative to the forearm 200, the palm 100 may be fixed.

The limb prosthesis 10 of the present embodiment does not include any active joint. In other words, the limb prosthesis 10 of the present embodiment does not adopt any driving motor or driving mechanism, and only has a simple mechanism, such that design cost, component cost, assembling cost and maintenance cost are greatly reduced, and most of the patients may easily afford to buy the limb prostheses, and malfunction probability of the limb prosthesis 10 is greatly decreased compared to the conventional mechanical limb prostheses with a motive power. Moreover, since the active motive power is not required, it is unnecessary to worry about the shortage of electricity. Since the palm 100 of the limb prosthesis 10 may perform flexion, extension and pronation and supination, it very helpful for the young children who need to learn and rehabilitate their proprioception. Moreover, since the angle of the palm 100 of the limb prosthesis 10 relative to the forearm 200 may be fixed, motion demands meeting the needs of a lot of daily life may be provided, for example, eating, washing clothes, choosing appropriate clothes, combing, keeping balance, wearing clothes, bathing, walking, shifting position (for example, from a bed to a wheelchair), etc., and certainly including assistive functions of basic motions such as a kneeling posture, a crawling posture, a lying posture, etc., of infants. Regarding the state of FIG. 1, it is similar to a state of an infant in the lying posture.

In the present embodiment, the wrist joint 500 allows the palm 100 to rotate and fix relative to the forearm 200 around the extending direction D10. In other words, the palm 100 of the limb prosthesis 10 may perform pronation and supination as that does of a healthy person. Moreover, after the palm 100 of the limb prosthesis 10 is pronated and supinated to a desired rotation angle relative to the forearm 200, the palm 100 may be fixed. In this way, the convenience of the user of the limb prosthesis 10 in life is further enhanced.

Figure 2:
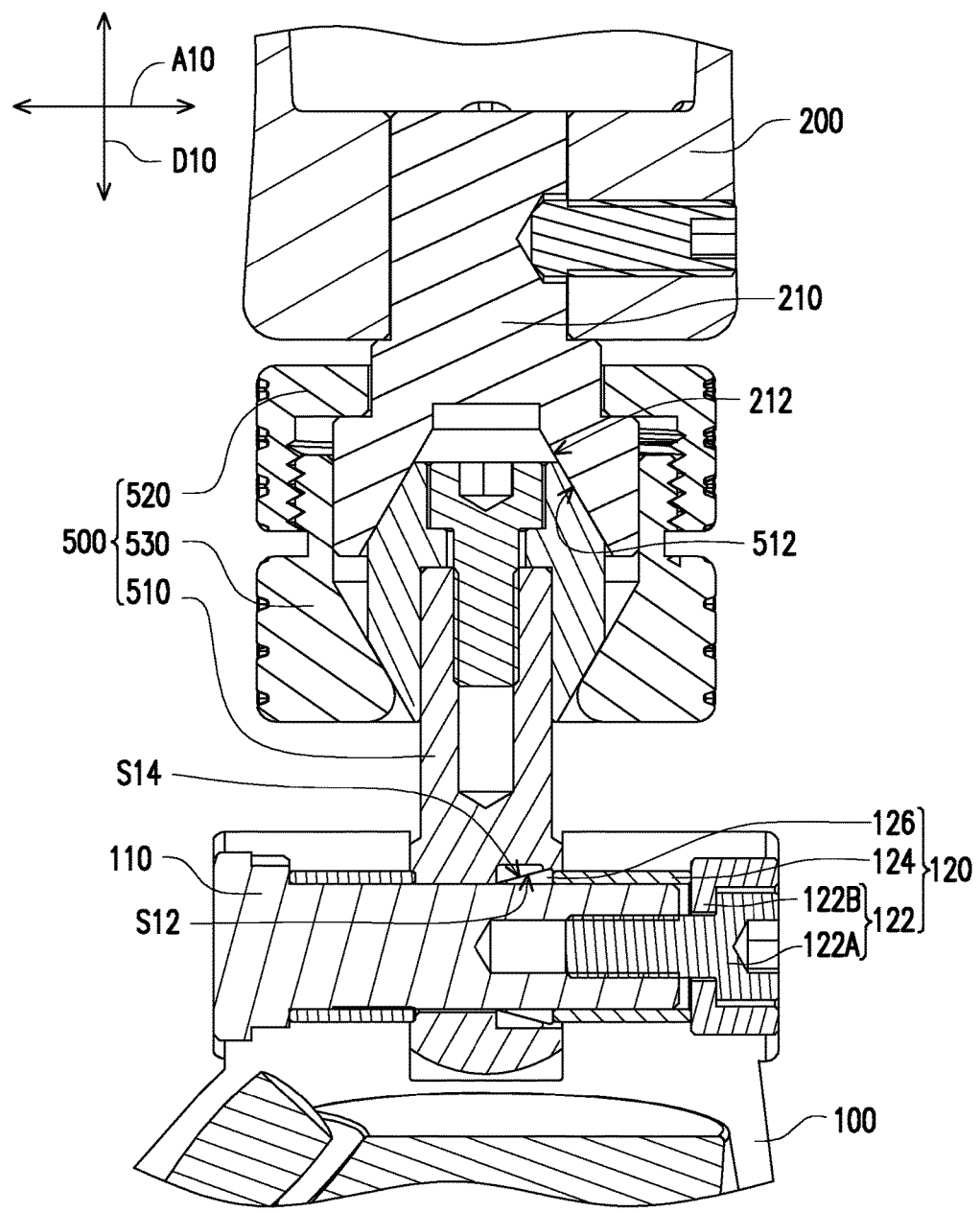
FIG. 2 is a cross-sectional view showing a wrist joint of the limb prosthesis of FIG. 1.

FIG. 2 is a cross-sectional view showing a wrist joint of the limb prosthesis of FIG. 1. Referring to FIG. 2, the forearm 200 has a second connecting rod 210, and the second connecting rod 210 has a connecting-rod wedge surface 212. The wrist joint 500 includes a first connecting rod 510 and an adjusting knob 520. The first connecting rod 510 has a contact surface 512. The adjusting knob 520 may be movably assembled to the first connecting rod 510. In other words, under the state that the adjusting knob 520 is maintained to be connected to the first connecting rod 510, a distance between the adjusting knob 520 and the first connecting rod 510 may be adjusted. The second connecting rod 210 penetrates through the adjusting knob 520 to contact the contact surface 512 of the first connecting rod 510 via the connecting-rod wedge surface 212. Since the part of the second connecting rod 210 having the connecting-rod wedge surface 212 is larger than an opening of the adjusting knob 520, the second connecting rod 210 cannot escape from the adjusting knob 520, and the adjusting knob 520 may drive the second connecting rod 210 to move. By adjusting the distance between the adjusting knob 520 and the first connecting rod 510, a magnitude of a forward force between the connecting-rod wedge surface 212 and the contact surface 512 is adjusted, such that the first connecting rod 510 is fixed or rotatable relative to the second connecting rod 210. Therefore, the wrist joint 500 may drive the palm 100 to pronate and supinate relative to the forearm 200.

To be specific, when the distance between the adjusting knob 520 and the first connecting rod 510 is enlarged, a distance between the second connecting rod 210 and the first connecting rod 510 is also enlarged, and the forward force between the connecting-rod wedge surface 212 and the contact surface 512 is reduced or even the two parts are separated, so that the first connecting rod 510 may be rotated relative to the second connecting rod 210. Namely, the wrist joint 500 may now rotate relative to the forearm 200, and the palm 100 also rotates relative to the forearm 200 around with the wrist joint 500.

Conversely, when the distance between the adjusting knob 520 and the first connecting rod 510 is reduced, the second connecting rod 210 is pushed by the adjusting knob 520 to closely press the first connecting rod 510, such that the forward force between the connecting-rod wedge surface 212 and the contact surface 512 is enlarged. Therefore, rotation of the first connecting rod 510 relative to the second connecting rod 210 is resisted by a friction caused by the forward force between the connecting-rod wedge surface 212 and the contact surface 512, such that an effect of fixing a relative position of the wrist joint 500 and the forearm 200 is achieved, and the palm 100 is fixed relative to the forearm 200 and cannot be pronated or supinated.

The contact surface 512 of the first connecting rod 510 of the wrist joint 500 of the present embodiment presents a wedge shape, so that the friction caused by the forward force between the connecting-rod wedge surface 212 and the contact surface 512 may be relatively large to improve the fixing effect of the palm 100 relative to the forearm 200. In FIG. 2, the connecting-rod wedge surface 212 and the contact surface 512 are presented in a cross-sectional view, and actually the connecting-rod wedge surface 212 and the contact surface 512 may be presented in form of a conical surface.

The wrist joint 500 of the present embodiment may further include a bearing seat 530 for assembling to the adjusting knob 520. The first connecting rod 510 penetrates through the bearing seat 530. Since the part of the first connecting rod 510 having the contact surface 512 is larger than an opening of the bearing seat 530, the first connecting rod 510 cannot escape from the bearing seat 530, and the adjusting knob 520 may drive the first connecting rod 510 to move. The bearing seat 530 and the adjusting knob 520 commonly combine the first connecting rod 510 and the second connecting rod 210 together.

To be specific, when the distance between the bearing seat 530 and the adjusting knob 520 is enlarged, the distance between the second connecting rod 210 and the first connecting rod 510 is also enlarged, and the forward force between the connecting-rod wedge surface 212 and the contact surface 512 is reduced or even the two parts are separated, so that the first connecting rod 510 may rotate relative to the second connecting rod 210. Namely, now the wrist joint 500 may rotate relative to the forearm 200, and the palm 100 also rotates relative to the forearm 200 around with the wrist joint 500.

Conversely, when the distance between the bearing seat 530 and the adjusting knob 520 is reduced, the second connecting rod 210 is pushed by the adjusting knob 520 to closely press the first connecting rod 510, and the first connecting rod 510 is also pushed by the bearing seat 530 to closely press the second connecting rod 210, such that the forward force between the connecting-rod wedge surface 212 and the contact surface 512 is enlarged. Therefore, rotation of the first connecting rod 510 relative to the second connecting rod 210 is resisted by the friction caused by the forward force between the connecting-rod wedge surface 212 and the contact surface 512, such that the effect of fixing a relative position of the wrist joint 500 and the forearm 200 is achieved, and the palm 100 is fixed relative to the forearm 200 and cannot be pronated or supinated.

In the present embodiment, the bearing seat 530 and the adjusting knob 520 are assembled through screw locking, though the disclosure is not limited thereto. The bearing seat 530 and the first connecting rod 510 of the present embodiment are independent components, though in other embodiment, the bearing seat 530 and the first connecting rod 510 may also be integrated into a single component as long as rotation of the first connecting rod 510 relative to the second connecting rod 210 is not influenced.

In the present embodiment, the wrist joint 500 of the present embodiment includes the first connecting rod 510. The palm 100 has a pivot 110 and a lock set 120. The first connecting rod 510 is connected to the forearm 200. The pivot 110 rotatably penetrates through the first connecting rod 510. In other words, the palm 100 may rotate relative to the wrist joint 500 around the pivot 110, and the pivot 110 is parallel to the aforementioned axial direction A10. The lock set 120 is locked to the pivot 110. A first wedge surface S12 of the lock set 120 is used for contacting a second wedge surface S14 of the first connecting rod 510. By adjusting a distance between the lock set 120 and the pivot 110, a magnitude of a forward force between the first wedge surface S12 and the second wedge surface S14 is adjusted, such that the palm 100 is fixed or rotatable relative to the first connecting rod 510. The pivot 110 and the lock set 120 are all a part of the palm 100, so that when the pivot 110 and the lock set 120 are rotated or fixed, the entire palm 100 is accordingly rotated or fixed. In this way, the palm 100 may be flexed or extended relative to the wrist joint 500 and the forearm 200.

To be specific, when the distance between the lock set 120 and the pivot 110 is enlarged, the forward force between the first wedge surface S12 and the second wedge surface S14 may be decreased or even the two parts are separated, so that the first connecting rod 510 may be rotated relative to the pivot 110. Namely, now the palm 100 may be rotated relative to the wrist joint 500.

Conversely, when the distance between the lock set 120 and the pivot 110 is shortened, the forward force between the first wedge surface S12 and the second wedge surface S14 is increased. Therefore, rotation of the first connecting rod 510 relative to pivot 110 is resisted by a friction caused by the forward force between the first wedge surface S12 and the second wedge surface S14, such that an effect of fixing a relative position of the first connecting rod 510 and the pivot 110 is achieved, and the palm 100 is fixed relative to the wrist joint 500 and cannot be flexed or extended.

The lock set 120 of the present embodiment includes an adjusting screw 122, a tightening ring 124 and a wedge ring 126. The adjusting screw 122 is locked to the pivot 110. The tightening ring 124 sleeves the pivot 110. The wedge ring 126 sleeves the pivot 110 and has the first wedge surface S12. When the distance between the adjusting screw 122 and the pivot 110 is adjusted, the adjusting screw 122 allows the wedge ring 126 to move forward or allows the wedge ring 126 to retreat. The adjusting screw 122 pushes the wedge ring 126 to move forward or allows the wedge ring 126 to retreat through the tightening ring 124. In other words, the tightening ring 124 may be leaned closely against the wedge ring 126 or loosed from the wedge ring 126. In other embodiment, the tightening ring 124 may be a part of the adjusting screw 122 instead of applying two components as that does in the present embodiment, and the adjusting screw 122 may directly push the wedge ring 126 to move forward or allow the wedge ring 126 to retreat. In still another embodiment, the tightening ring 124 may be a part of the wedge ring 126 instead of applying two components as that does in the present embodiment. Alternatively, configuration of the tightening ring 124 may be omitted, and the adjusting screw 122 is directly used for pushing the wedge ring 126 having the wedge surface.

A material of the wedge ring 126 may be a polymer material (for example, nylon or polyoxymethylene (POM)) or a metal material (for example, aluminium alloy, medium carbon steel) or other proper materials. A material of the tightening ring 124 may be a polymer material (for example, nylon or POM) or a metal material (for example, aluminium alloy, medium carbon steel, etc.) or other proper materials. A material of the second wedge surface S14 of the first connecting rod 510 of the present embodiment may be a polymer material (for example, nylon or POM) or a metal material (for example, aluminium alloy, medium carbon steel, etc.) or other proper materials, and the material of the second wedge surface S14 may be different to the material of other parts of the first connecting rod 510. The adjusting screw 122 of the present embodiment may include a screw 122A and a spacer bearing seat 122B. The screw 122A is locked to the pivot 110, and the screw 122A is used for pushing the spacer bearing seat 122B to move forward or allowing the spacer bearing seat 122B to retreat. The spacer bearing seat 122B is used for pushing the tightening ring 124 to move forward or allowing the tightening ring 124 to retreat.

Figure 3:
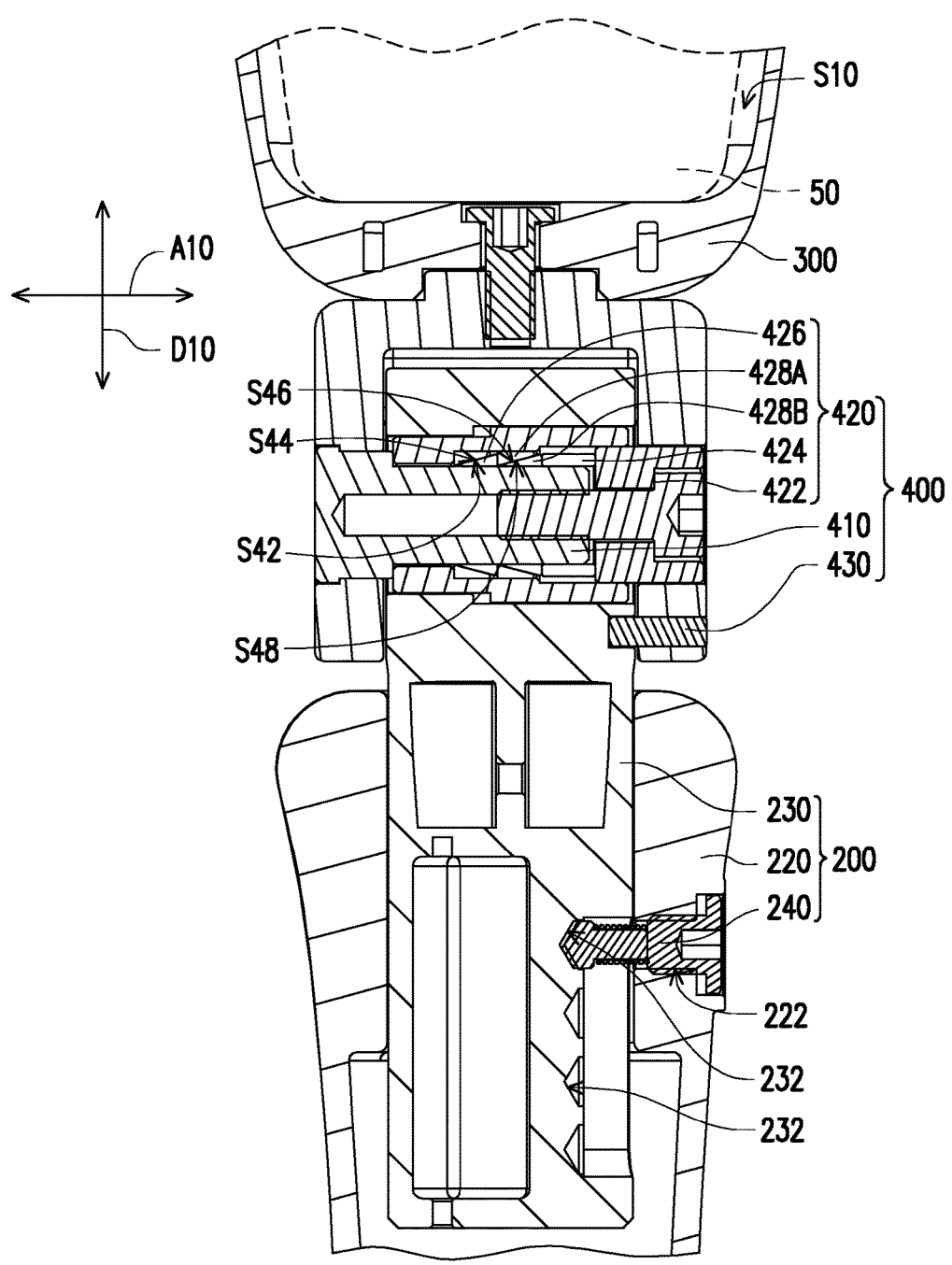
FIG. 3 is a cross-sectional view showing an elbow joint of the limb prosthesis of FIG. 1.

FIG. 3 is a cross-sectional view showing an elbow joint of the limb prosthesis of FIG. 1. Referring to FIG. 3, the elbow joint 400 allows the forearm 200 to rotate or fix relative to the upper arm 300 around the axial direction A10. In other words, the forearm 200 of the limb prosthesis 10 may perform flexion and extension relative to the upper arm 300 as that does of a healthy person. Moreover, after the forearm 200 of the limb prosthesis 10 is flexed or extended to a desired rotation angle relative to the upper arm 300, the forearm 200 may be fixed. In this way, the convenience of the user of the limb prosthesis 10 in life is further enhanced.

In the present embodiment, the elbow joint 400 is fixed to the upper arm 300 and has a pivot 410 and a lock set 420. The pivot 410 may rotatably penetrate through the forearm 200. In other words, the forearm 200 may rotate relative to the elbow joint 400 and the upper arm 300 around the pivot 410, and the pivot 410 is parallel to the aforementioned axial direction A10. The lock set 420 is locked to the pivot 410. A first wedge surface S42 of the lock set 420 is used for contacting a second wedge surface S44 of the forearm 200. By adjusting a distance between the lock set 420 and the pivot 410, a magnitude of a forward force between the first wedge surface S42 and the second wedge surface S44 is adjusted, such that the forearm 200 is fixed or rotatable relative to the upper arm 300. In this way, the forearm 200 may be flexed or extended relative to the elbow joint 400 and the upper arm 300.

To be specific, when the distance between the lock set 420 and the pivot 410 is enlarged, the forward force between the first wedge surface S42 and the second wedge surface S44 may be decreased or even the two parts are separated, so that the forearm 200 may be rotated relative to the pivot 410. Namely, now the forearm 200 may be flexed or extended relative to the elbow joint 400 and the upper arm 300.

Conversely, when the distance between the lock set 420 and the pivot 410 is shortened, the forward force between the first wedge surface S42 and the second wedge surface S44 is increased. Therefore, rotation of the forearm 200 relative to pivot 410 is resisted by a friction caused by the forward force between the first wedge surface S42 and the second wedge surface S44, such that an effect of fixing a relative position of the forearm 200 and the pivot 410 is achieved, and the forearm 200 is fixed relative to the elbow joint 400 and the upper arm 300 and cannot be flexed or extended.

The lock set 420 of the present embodiment includes an adjusting screw 422, a tightening ring 424 and a first wedge ring 426. The adjusting screw 422 is locked to the pivot 410. The tightening ring 424 sleeves the pivot 410. The first wedge ring 426 sleeves the pivot 410 and has the first wedge surface S42. When the distance between the adjusting screw 422 and the pivot 410 is adjusted, the adjusting screw 422 allows the first wedge ring 426 to move forward or allows the first wedge ring 426 to retreat. The adjusting screw 422 pushes the first wedge ring 426 to move forward or allows the first wedge ring 426 to retreat through the tightening ring 424. In other words, the tightening ring 424 may be leaned closely against the first wedge ring 426 or loosed from the first wedge ring 426. In other embodiment, the tightening ring 424 may be a part of the adjusting screw 422 instead of applying two components as that does in the present embodiment, and the adjusting screw 422 may directly push the first wedge ring 426 to move forward or allow the first wedge ring 426 to retreat. In still another embodiment, the tightening ring 424 may be a part of the first wedge ring 426 instead of applying two components as that does in the present embodiment. Alternatively, configuration of the tightening ring 424 may be omitted, and the adjusting screw 422 is directly used for pushing the first wedge ring 426 having the wedge surface.

A material of the first wedge ring 426 may be a polymer material (for example, nylon or POM) or a metal material (for example, aluminium alloy, medium carbon steel) or other proper materials. A material of the tightening ring 424 may be a polymer material (for example, nylon or POM) or a metal material (for example, aluminium alloy, medium carbon steel, etc.) or other proper materials. A material of the second wedge surface S44 of the forearm 200 of the present embodiment may be a polymer material (for example, nylon or POM) or a metal material (for example, aluminium alloy, medium carbon steel, etc.) or other proper materials, and the material of the second wedge surface S44 may be different to the material of other parts of the forearm 200. Composition of the adjusting screw 422 of the present embodiment may be similar to that of the adjusting screw 122 of FIG. 2, and detail thereof is not repeated.

The lock set 420 of the present embodiment further includes a second wedge ring 428A and a third wedge ring 428B, and the two wedge rings 428A and 428B all sleeve the pivot 410 and are located between the tightening ring 424 and the first wedge ring 426. In other words, the tightening ring 424 pushes the first wedge ring 426 to move forward or allows the first wedge ring 426 to retreat through the second wedge ring 428A and the third wedge ring 428B. A third wedge surface S46 of the second wedge ring 428A is used for contacting a fourth wedge surface S48 of the third wedge ring 428B. The second wedge ring 428A and the third wedge ring 428B may also be used for fixing the relative position of the forearm 200 and the pivot 410. A material of the second wedge ring 428A and the third wedge ring 428B may be a polymer material (for example, nylon or POM) or a metal material (for example, aluminium alloy, medium carbon steel, etc.) or other proper materials. The number of the wedge rings used in the lock set 420 of the present embodiment may be more or less, and the number of the wedge rings used in the lock set 120 of FIG. 2 may be more.

Figure 4:
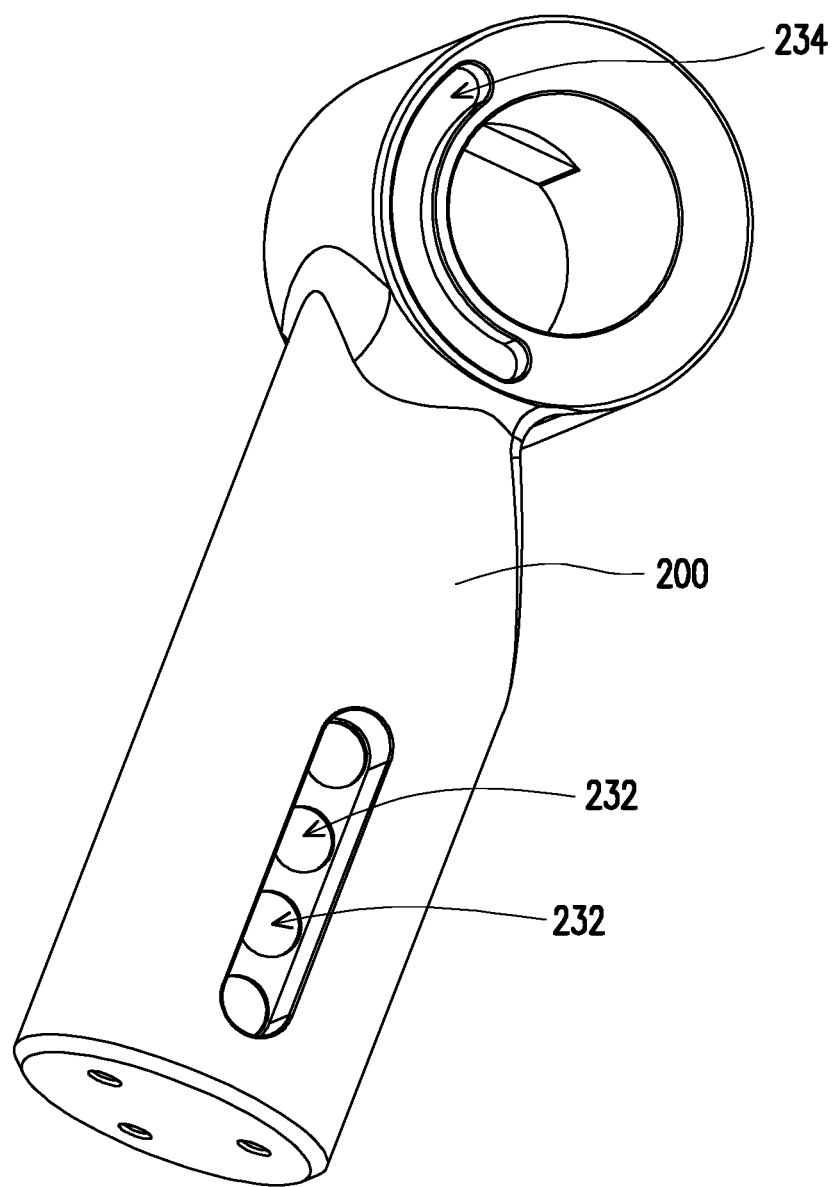
FIG. 4 is a partial schematic diagram of a forearm of the limb prosthesis of FIG. 1.

FIG. 4 is a partial schematic diagram of the forearm of the limb prosthesis of FIG. 1. Referring to FIG. 3 and FIG. 4, the forearm 200 of the present embodiment includes a sleeve 220, a rod 230 and a positioning pin 240. The sleeve 220 has an opening 222. The rod 230 is slidably disposed in the sleeve 220 and has a plurality of positioning slots 232. The positioning pin 240 penetrates through the opening 222 and is engaged to one of the positioning slots 232. Base on the design that the rod 230 is slidably disposed in the sleeve 220, an overall length of the forearm 200 constructed by the rod 230 and the sleeve 220 is adjustable. Moreover, the overall length of the forearm 200 may be fixed through an engaging relationship between the positioning pin 240 and the opening 222. Therefore, when a child uses the limb prosthesis 10 of the present embodiment, the overall length of forearm 200 may be adjusted along with the growth of age without spending money to buy a new conventional limb prosthesis due to usage of the conventional fixed limb prosthesis, so that a financial burden for using the limb prosthesis is greatly reduced, and medical care for young children requiring the limb prosthesis is created.

The elbow joint 400 of the present embodiment further has a rotation pin 430. The forearm 200 has a sliding slot 234. One end of the rotation pin 430 is adapted to slide within the sliding slot 234. A rotating range of the upper arm 300 relative to the forearm 200 is limited through collaboration of the sliding slot 234 and the rotation pin 430. For example, the sliding slot 234 may be a ¼ circle, so that the upper arm 300 may only be rotated by 90 degrees relative to the forearm 200. In this way, even if the pivot 410 and the forearm 200 are accidentally loosened, over rotation of the upper arm 300 relative to the forearm 200 is still avoided, so as to provide a better protection mechanism to the user.

Figure 5:
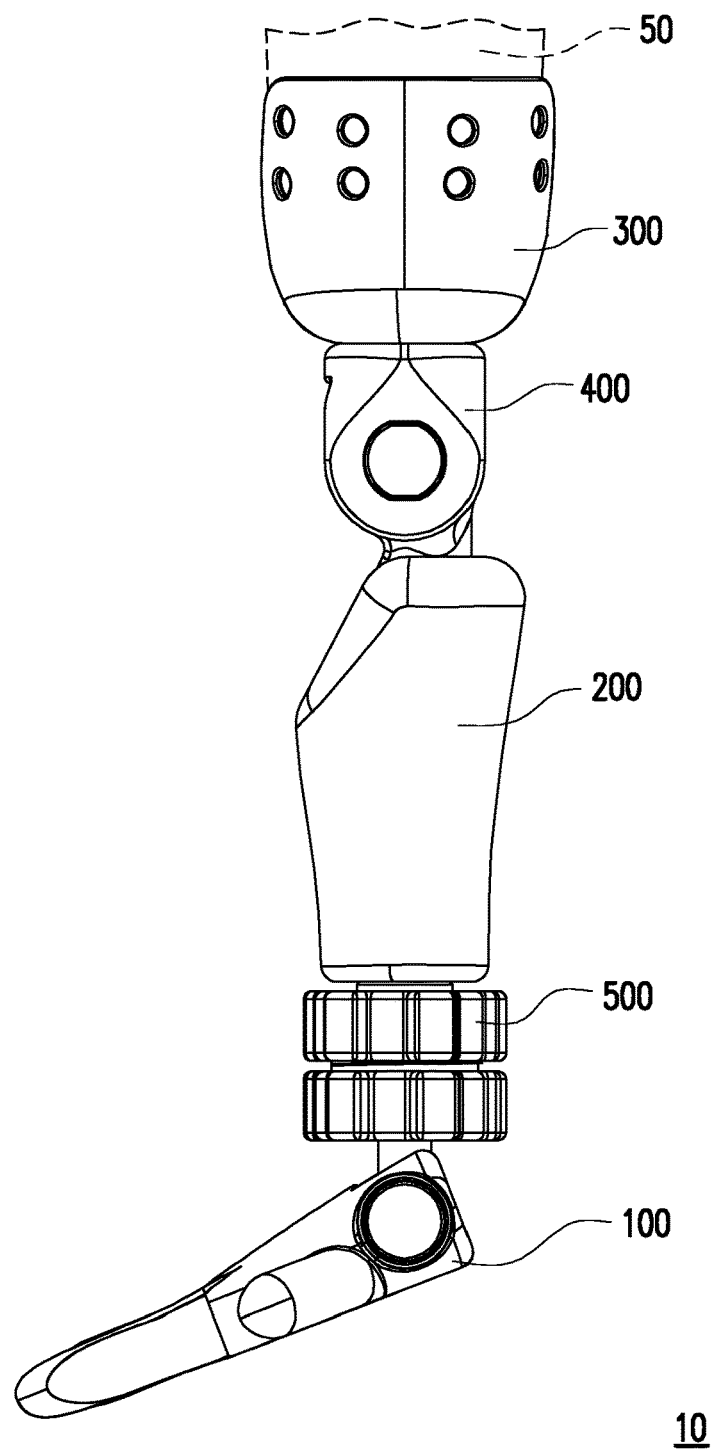
FIG. 5 and FIG. 6 are schematic diagrams of the limb prosthesis of FIG. 1 set in two different postures.
Figure 6:
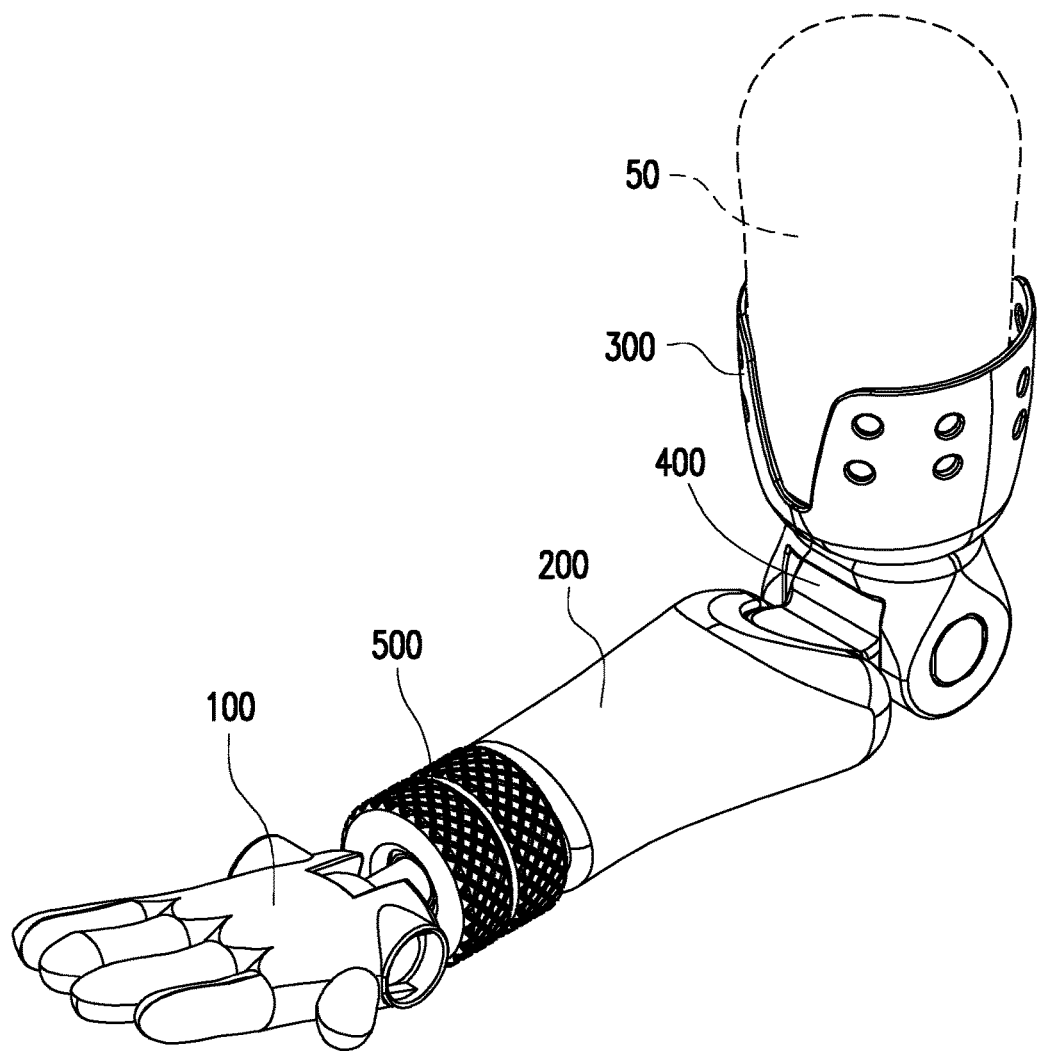

FIG. 5 and FIG. 6 are schematic diagrams of the limb prosthesis of FIG. 1 set in two different postures. Referring to FIG. 5, the palm 100 of the limb prosthesis 10 of the present embodiment may be flexed relative to the wrist joint 500 and the forearm 200, and the palm 100 may provide a solid supporting force, which is adapted to the needs of the child in a sitting posture. Referring to FIG. 6, the forearm 200 of the limb prosthesis 10 of the present embodiment may be flexed relative to the upper arm 300, and the elbow joint 400 may provide the solid supporting force, which is adapted to the needs of the child leaning on the ground by using hands and elbows. Therefore, the palm 100 of the limb prosthesis 10 of the present embodiment may be flexed, extended, pronated and supinated relative to the forearm 200, and the forearm 200 may be flexed and extended relative to the upper arm 300, which may provide great usage convenience.

Figure 7:
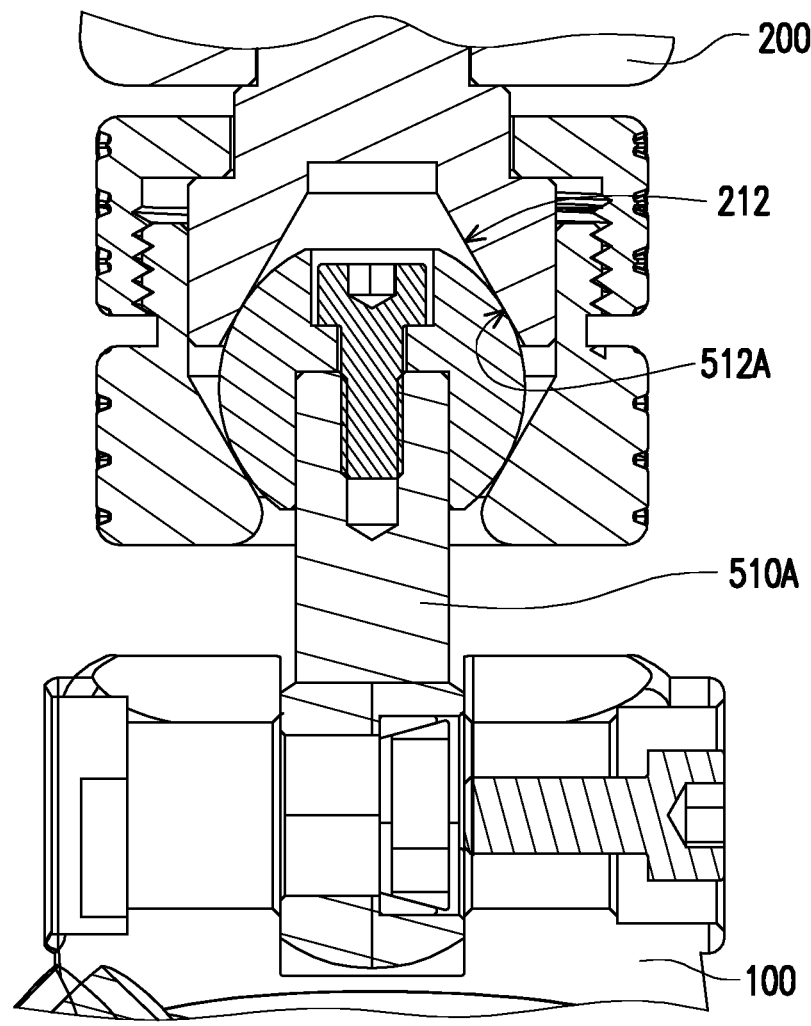
FIG. 7 is a cross-sectional view of a limb prosthesis at the wrist joint according to another embodiment of the disclosure.

FIG. 7 is a cross-sectional view of the limb prosthesis at the wrist joint according to another embodiment of the disclosure. Referring to FIG. 7, the wrist joint of the limb prosthesis of the present embodiment is basically the same with the wrist joint 500 of FIG. 2, and a difference there between is only that the contact surface 512A of the first connecting rod 510A of the present embodiment presents a ball shape. Certainly, the contact surface of the first connecting rod may also be other shapes, which is not limited by the disclosure.

Figure 8:
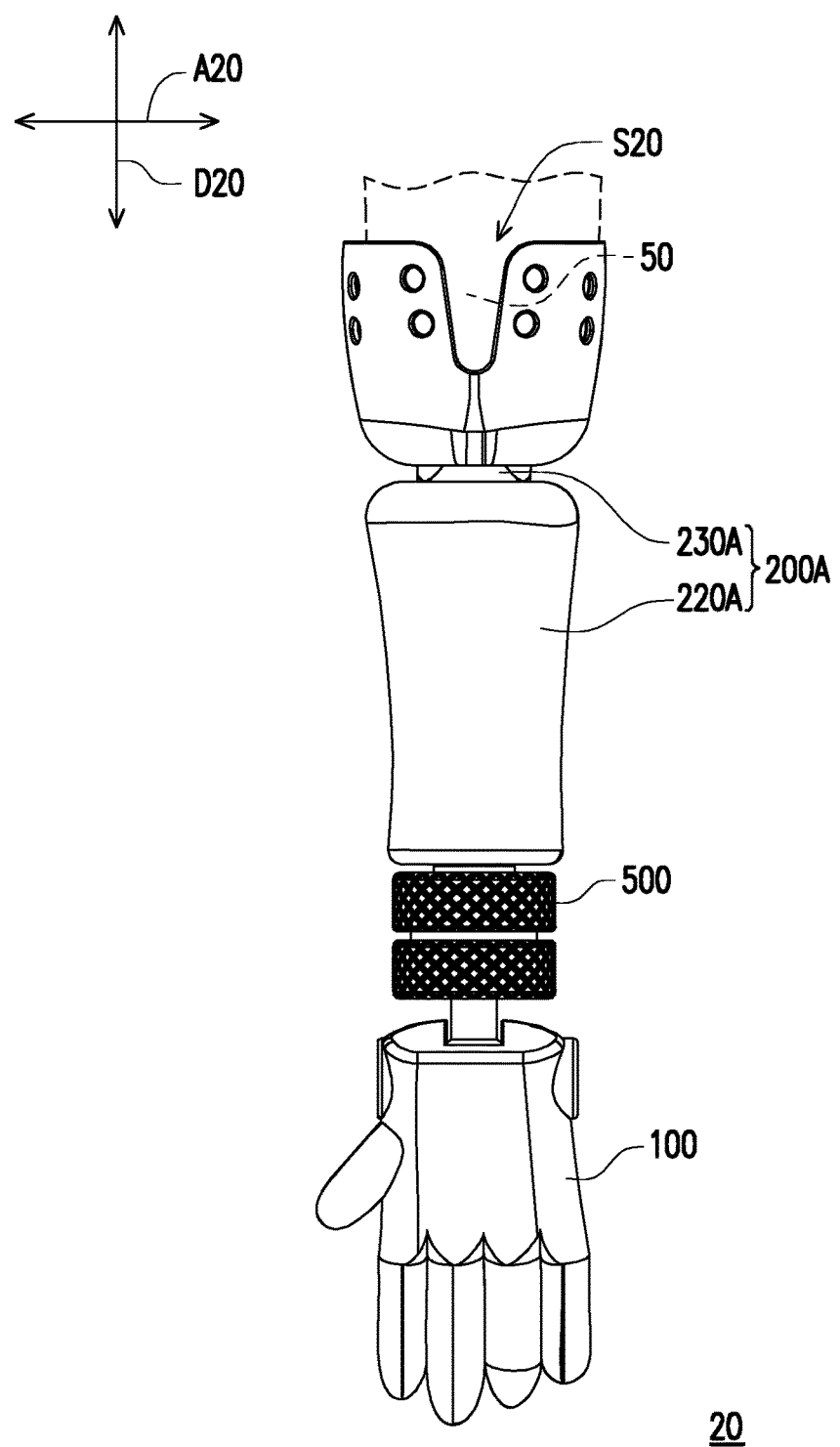
FIG. 8 is a schematic diagram of a limb prosthesis according to another embodiment of the disclosure.

FIG. 8 is a schematic diagram of a limb prosthesis according to another embodiment of the disclosure. Referring to FIG. 8, the limb prosthesis 20 of the disclosure is basically similar to the limb prosthesis 10 of FIG. 1, and a difference there between is that the limb prosthesis 20 of the present embodiment only includes the palm 100, the forearm 200A and the wrist joint 500 without including the elbow joint and the upper arm. Moreover, the forearm 200A of the present embodiment has a socket S20. In other words, the limb prosthesis 20 of the present embodiment is adapted to a situation that the upper arm of the patient is complete and the forearm of the patient only has a residual limb. The wrist joint 500 of the present embodiment also connects the palm 100 to the forearm 200A. The palm 100 is adapted to rotate and fix relative to the forearm 200A through the wrist joint 500 around an axial direction A20, where the axial direction A20 is perpendicular to an extending direction D20 of the forearm 200A. Detailed designs of the palm 100, the forearm 200A and the wrist joint 500 of the present embodiment may be all the same with that of the embodiment of FIG. 2. Moreover, the forearm 200A of the present embodiment may also be similar to the forearm 200 of FIG. 3, i.e. the forearm 200A includes the sleeve 220A, the rod 230A and the positioning pin (not shown), and the rod 230A is slidably disposed in the sleeve 220A. Therefore, the overall length of the forearm 200A is also adjustable. The socket S20 is, for example, located at one end of the rod 230A.

In summary, in the limb prosthesis of the disclosure, the wrist joint rotated in a passive manner is provided in a simple mechanism design, which not only has a better usage convenience, but also has a low cost and good capability.

It will be apparent to those skilled in the art that various modifications and variations can be made to the structure of the disclosure without departing from the scope or spirit of the disclosure. In view of the foregoing, it is intended that the disclosure cover modifications and variations of this disclosure provided they fall within the scope of the following claims and their equivalents.

What is claimed is:

1. A limb prosthesis, comprising:
    a palm, having a first pivot and a first lock set;
    a forearm;
    an upper arm, having a socket;
    an elbow joint, connecting the forearm to the upper arm; and
    a wrist joint, connecting the palm to the forearm, wherein the wrist joint comprises a first connecting rod, the first connecting rod is connected to the forearm, the first pivot rotatably penetrates through the first connecting rod, the first lock set is locked to the first pivot, a first wedge surface of the first lock set is used for contacting a second wedge surface of the first connecting rod, and by adjusting a distance between the first lock set and the first pivot, a magnitude of a forward force between the first wedge surface and the second wedge surface is adjusted, such that the palm is fixed relative to the first connecting rod or rotatable around an axial direction, and the axial direction is perpendicular to an extending direction of the forearm.

2. The limb prosthesis as claimed in claim 1, wherein the forearm has a second connecting rod, the second connecting rod has a connecting-rod wedge surface, the first connecting rod has a contact surface, and the wrist joint further comprises:
    an adjusting knob, movably assembled to the first connecting rod, wherein the second connecting rod penetrates through the adjusting knob to contact the contact surface of the first connecting rod via the connecting-rod wedge surface, and by adjusting a distance between the adjusting knob and the first connecting rod, a magnitude of a forward force between the connecting-rod wedge surface and the contact surface is adjusted, such that the first connecting rod is fixed relative to the second connecting rod or rotatable around the extending direction.

3. The limb prosthesis as claimed in claim 2, wherein the contact surface presents a wedge shape or a ball shape.

4. The limb prosthesis as claimed in claim 2, wherein the wrist joint further comprises a bearing seat assembled to the adjusting knob, the first connecting rod penetrates through the bearing seat, and the bearing seat and the adjusting knob commonly combine the first connecting rod and the second connecting rod together.

5. The limb prosthesis as claimed in claim 1, wherein the first lock set comprises:
    an adjusting screw, locked to the first pivot; and
    a wedge ring, sleeving the first pivot and having the first wedge surface, wherein when a distance between the adjusting screw and the first pivot is adjusted, the adjusting screw allows the wedge ring to move forward or retreat.

6. The limb prosthesis as claimed in claim 1, wherein the elbow joint is fixed to the upper arm and has a second pivot and a second lock set, the second pivot rotatably penetrates through the forearm, the second lock set is locked to the second pivot, a third wedge surface of the second lock set is used for contacting a fourth wedge surface of the forearm, and by adjusting a distance between the second lock set and the second pivot, a magnitude of a forward force between the third wedge surface and the fourth wedge surface is adjusted, such that the forearm is fixed relative to the upper arm or rotatable around the axial direction perpendicular to the extending direction of the forearm.

7. The limb prosthesis as claimed in claim 6, wherein the second lock set comprises:
    an adjusting screw, locked to the second pivot; and
    a first wedge ring, sleeving the second pivot and having the third wedge surface, wherein when a distance between the adjusting screw and the second pivot is adjusted, the adjusting screw allows the first wedge ring to move forward or retreat.

8. The limb prosthesis as claimed in claim 7, wherein the second lock set further comprises a tightening ring, a second wedge ring and a third wedge ring sleeving the second pivot, the tightening ring is located between the adjusting screw and the first wedge ring, the second wedge ring and the third wedge ring are located between the tightening ring and the first wedge ring, and a fifth wedge surface of the second wedge ring is used for contacting a sixth wedge surface of the third wedge ring.

9. The limb prosthesis as claimed in claim 6, wherein the elbow joint further has a rotation pin, the forearm has a sliding slot, one end of the rotation pin is adapted to slide within the sliding slot, and a rotating range of the forearm relative to the upper arm is limited through collaboration of the sliding slot and the rotation pin.

10. The limb prosthesis as claimed in claim 1, wherein the forearm comprises:
    a sleeve, having an opening;
    a rod, slidably disposed in the sleeve and having a plurality of positioning slots; and
    a positioning pin, penetrating through the opening and engaged to one of the positioning slots.

11. A limb prosthesis, comprising:
    a palm, having a pivot and a lock set;
    a forearm, having a socket; and
    a wrist joint, connecting the palm to the forearm, wherein the wrist joint comprises a first connecting rod, the first connecting rod is connected to the forearm, the pivot rotatably penetrates through the first connecting rod, the lock set is locked to the pivot, a first wedge surface of the lock set is used for contacting a second wedge surface of the first connecting rod, by adjusting a distance between the lock set and the pivot, a magnitude of a forward force between the first wedge surface and the second wedge surface is adjusted, such that the palm is fixed relative to the first connecting rod or rotatable around an axial direction, and the axial direction is perpendicular to an extending direction of the forearm.

12. The limb prosthesis as claimed in claim 11, wherein the forearm has a second connecting rod, the second connecting rod has a connecting-rod wedge surface, the first connecting rod has a contact surface, and the wrist joint further comprises:
   an adjusting knob, movably assembled to the first connecting rod, wherein the second connecting rod penetrates through the adjusting knob to contact the contact surface of the first connecting rod via the connecting-rod wedge surface, and by adjusting a distance between the adjusting knob and the first connecting rod, a magnitude of a forward force between the connecting-rod wedge surface and the contact surface is adjusted, such that the first connecting rod is fixed relative to the second connecting rod or rotatable around the extending direction.

13. The limb prosthesis as claimed in claim 12, wherein the contact surface presents a wedge shape or a ball shape.

14. The limb prosthesis as claimed in claim 12, wherein the wrist joint further comprises a bearing seat assembled to the adjusting knob, the first connecting rod penetrates through the bearing seat, and the bearing seat and the adjusting knob commonly combine the first connecting rod and the second connecting rod together.

15. The limb prosthesis as claimed in claim 11, wherein the lock set comprises:
   an adjusting screw, locked to the pivot; and
   a wedge ring, sleeving the pivot and having the first wedge surface, wherein when a distance between the adjusting screw and the pivot is adjusted, the adjusting screw allows the wedge ring to move forward or retreat.

16. The limb prosthesis as claimed in claim 11, wherein the forearm comprises:
   a sleeve, having an opening;
   a rod, slidably disposed in the sleeve and having a plurality of positioning slots, wherein the socket is located at the rod or the sleeve; and
   a positioning pin, penetrating through the opening and engaged to one of the positioning slots.

* * * * *